United States Patent [19]

Woodruff

[11] Patent Number: 5,084,479
[45] Date of Patent: Jan. 28, 1992

[54] METHODS FOR TREATING NEURODEGENERATIVE DISEASES

[75] Inventor: Geoffrey N. Woodruff, Herts, United Kingdom

[73] Assignee: Warner-Lambert Company, Morris Plains, N.J.

[21] Appl. No.: 615,151

[22] Filed: Nov. 23, 1990

Related U.S. Application Data

[63] Continuation-in-part of Ser. No. 459,912, Jan. 2, 1990, abandoned.

[51] Int. Cl.$^5$ .............................................. A61K 31/215
[52] U.S. Cl. .................................................... 514/530
[58] Field of Search ........................................ 514/530

*Primary Examiner*—Stanley J. Friedman
*Attorney, Agent, or Firm*—Elizabeth M. Anderson

[57] ABSTRACT

The instant invention is novel uses of known cyclic amino acids. Such compounds as gabapentin are used for treating neurodegenerative disorders, perinatal asphyxia, *status epilepticus*, Alzheimer's Hungington's, Parkinson's, and Amyotrophic Lateral Sclerosis.

8 Claims, 13 Drawing Sheets

1 uM GLY & 10 uM STRY 10 uM GABA - P 1 uM GLY & 10 uM STRY

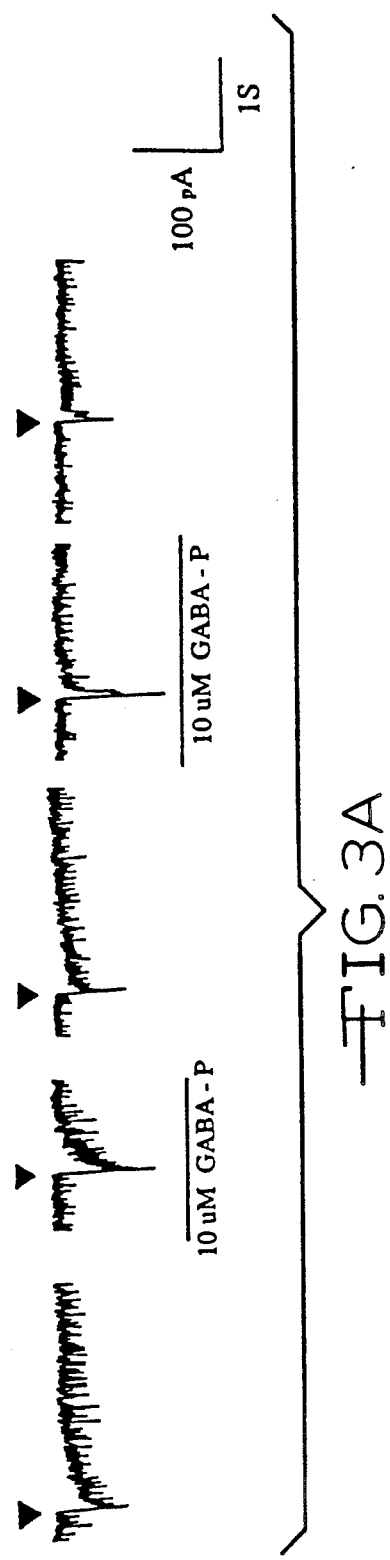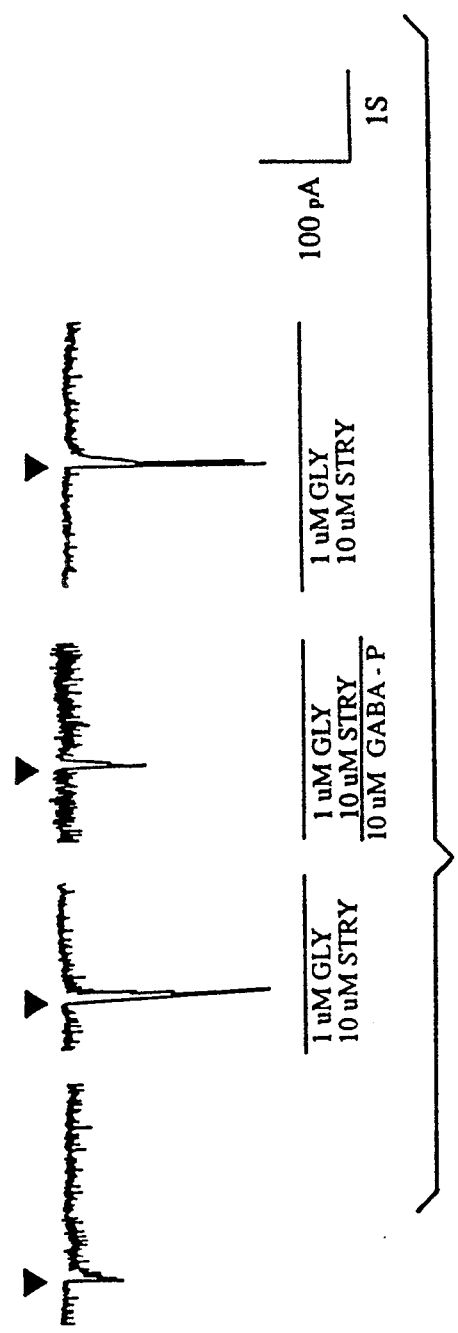
FIG. 3A
FIG. 3B

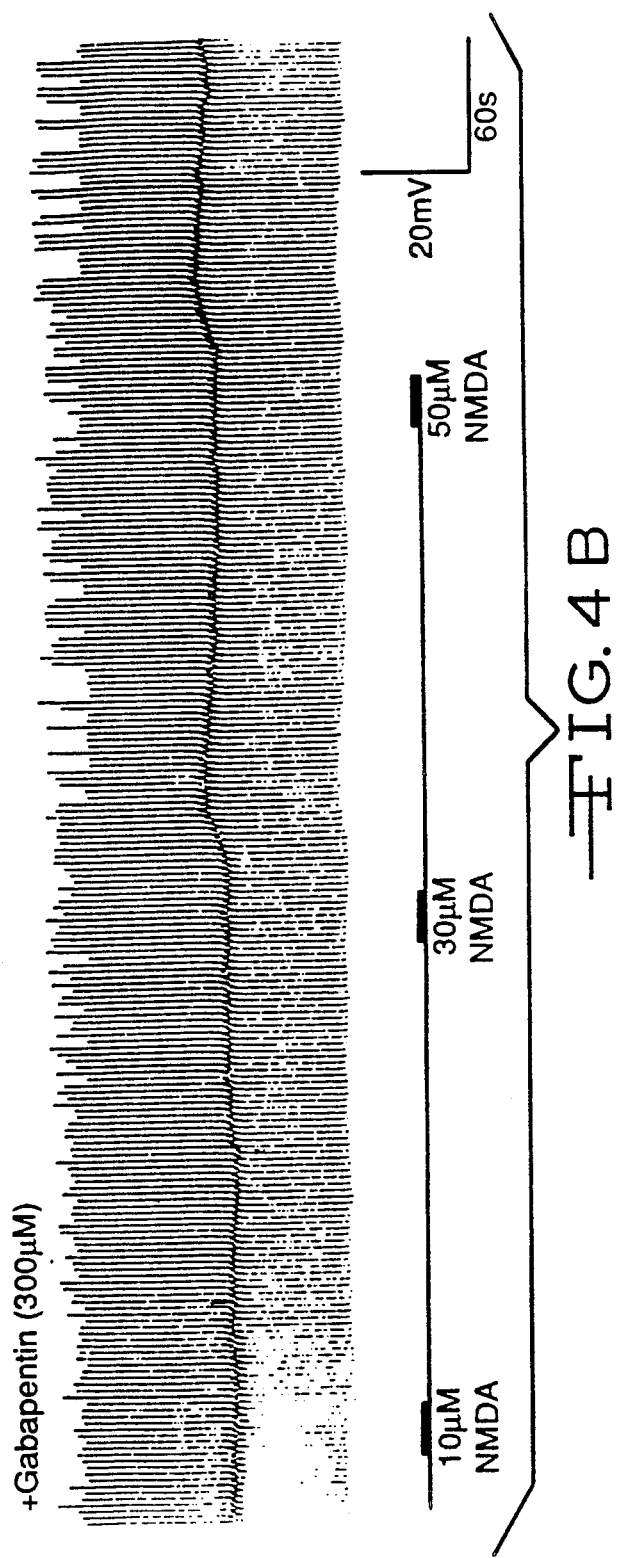

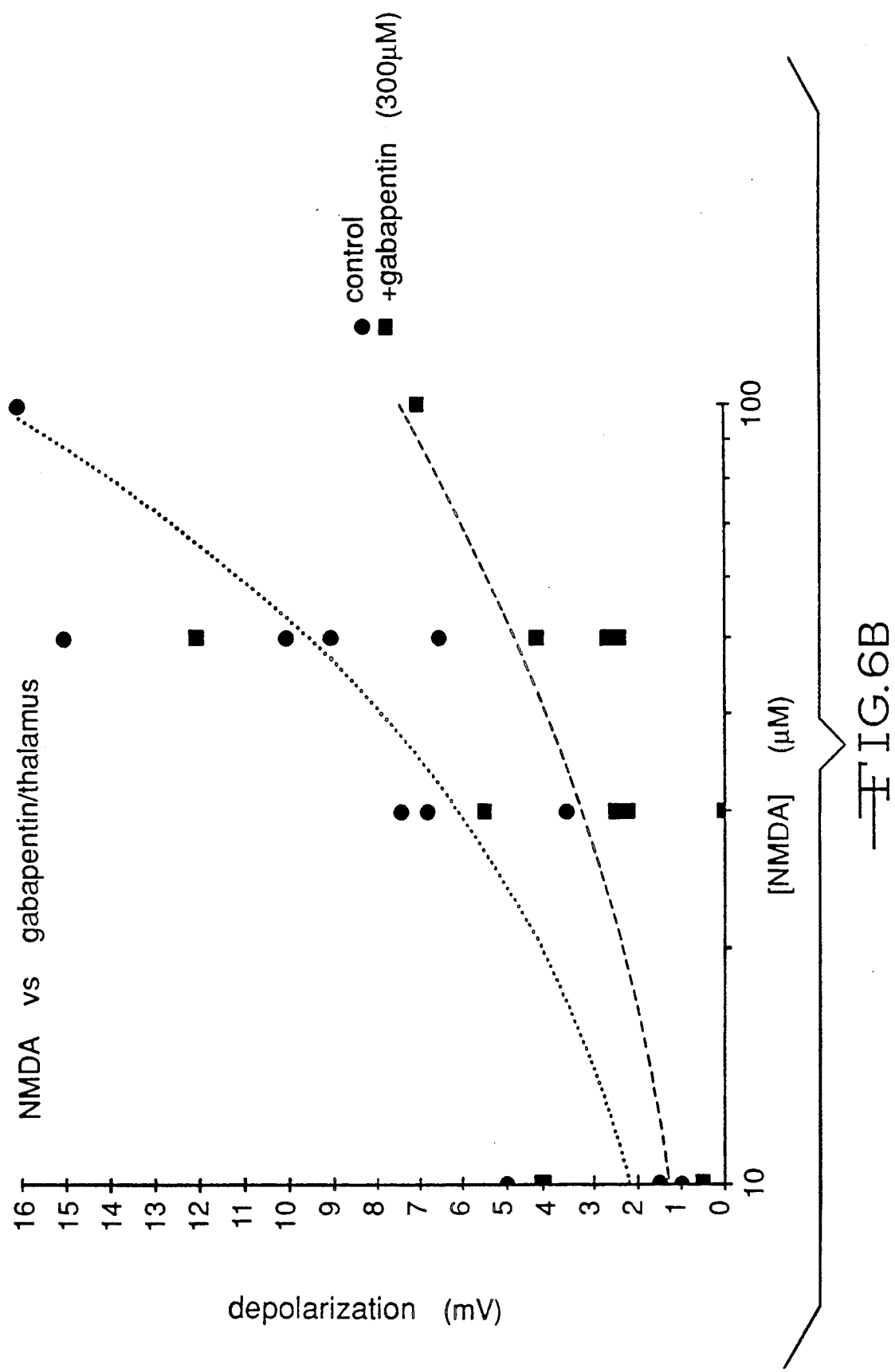

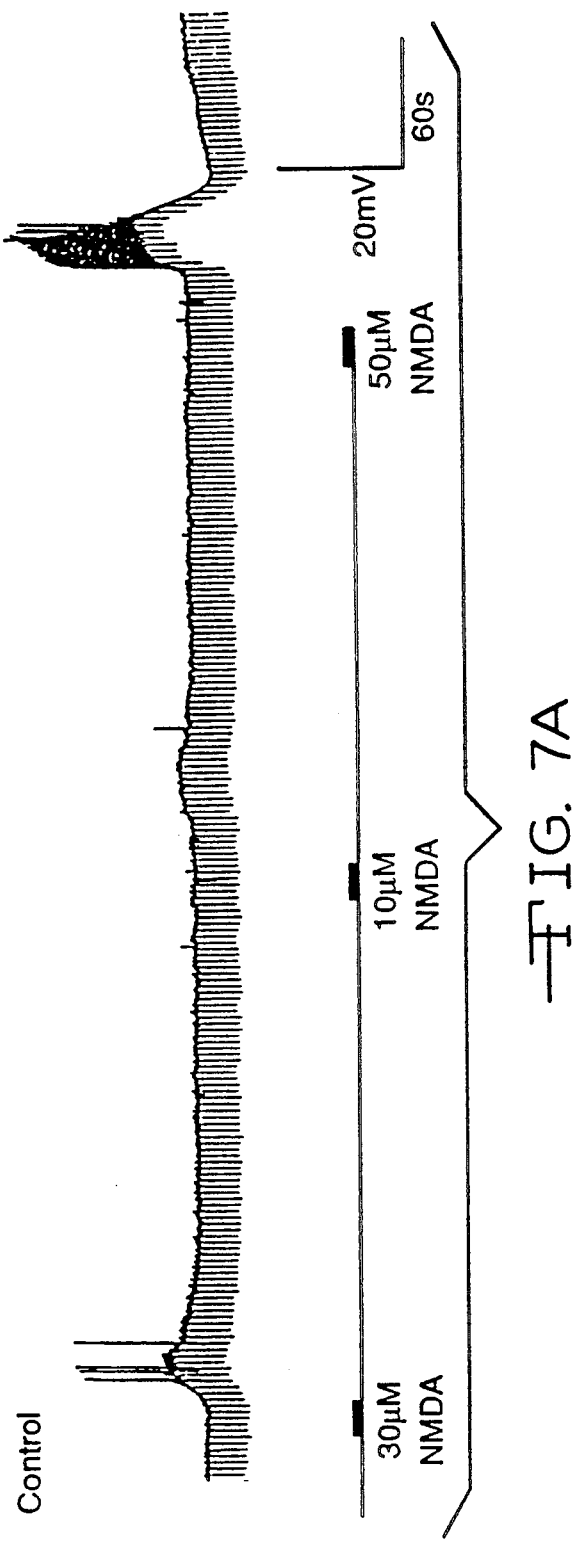

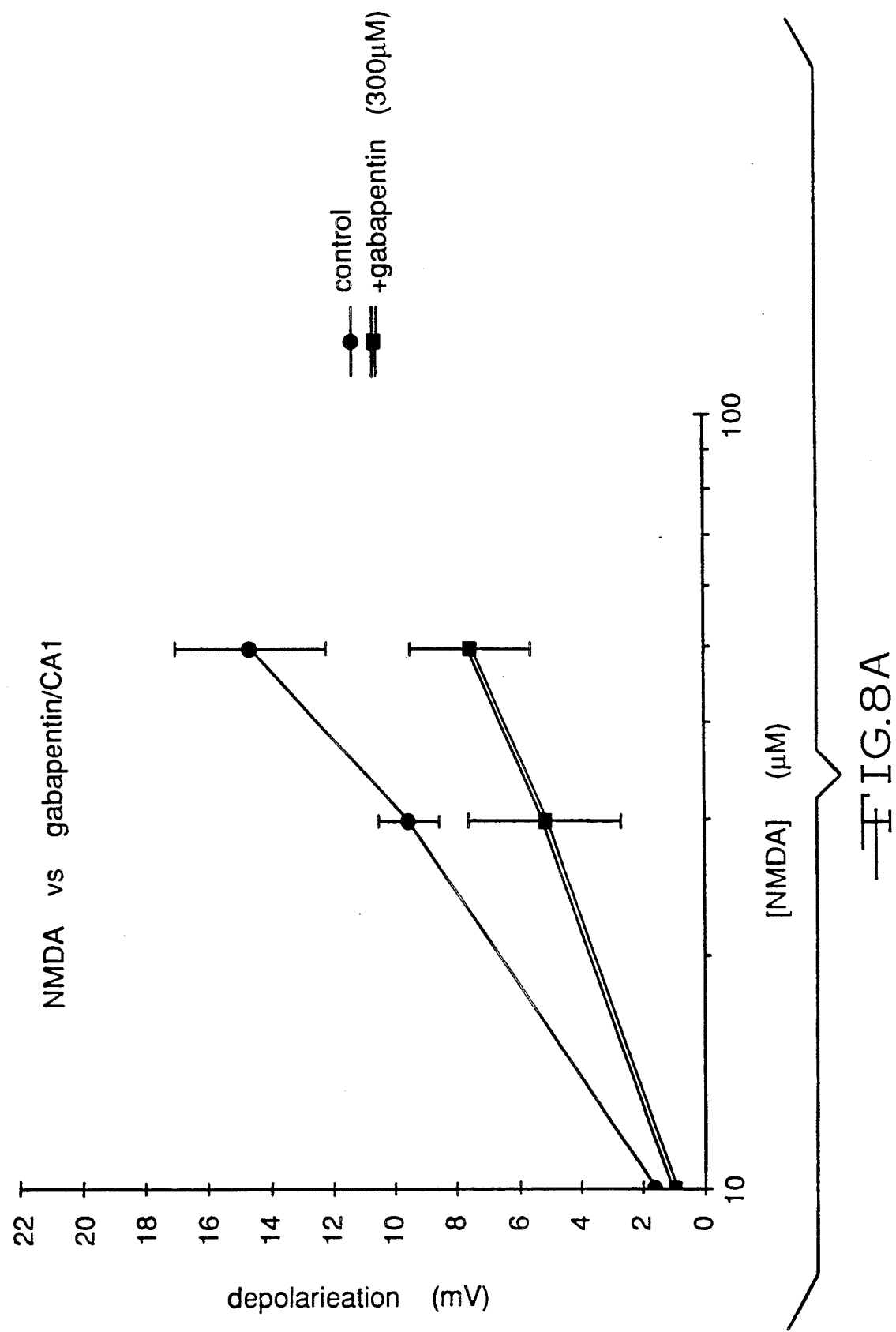

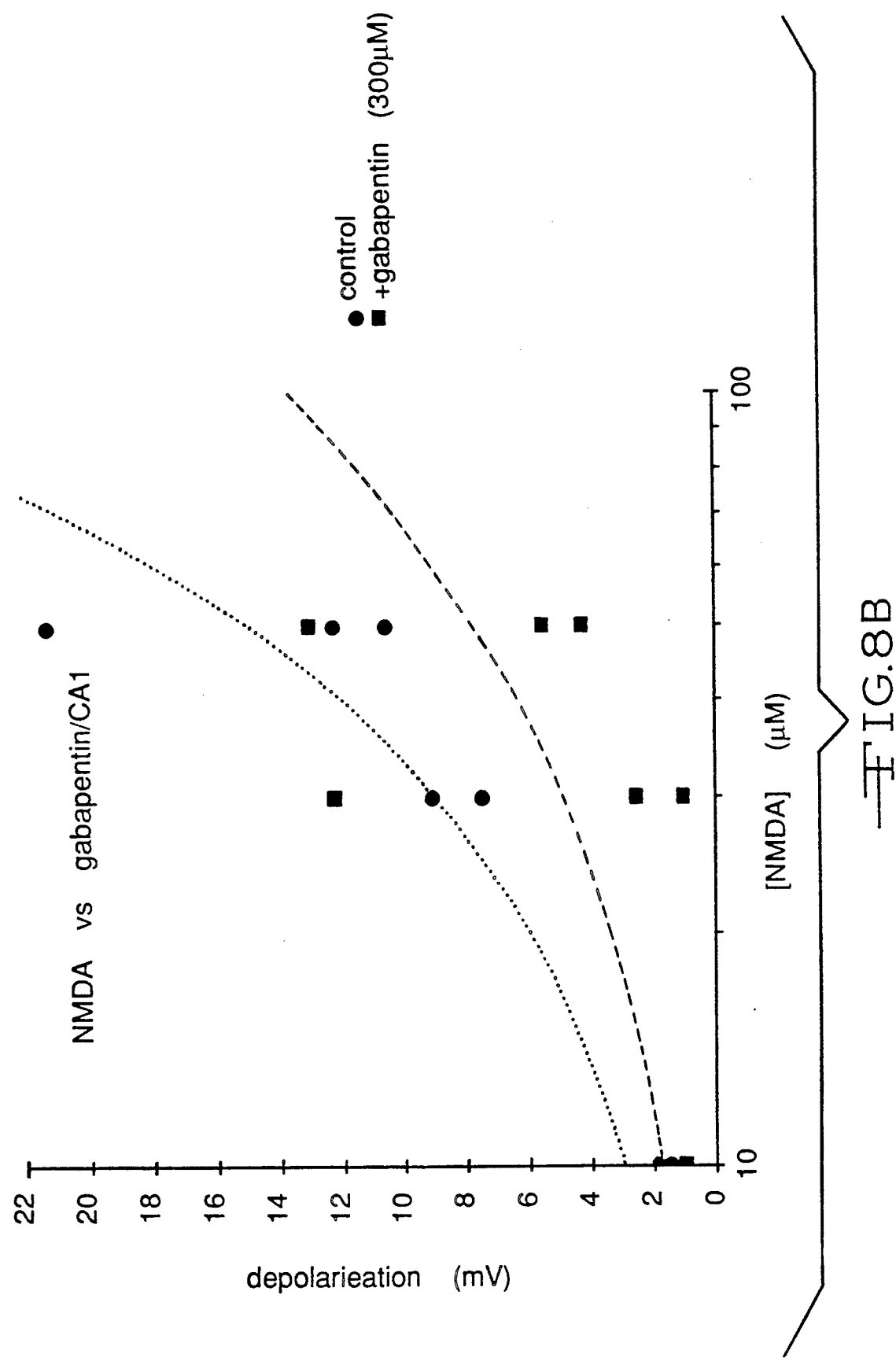

METHODS FOR TREATING NEURODEGENERATIVE DISEASES

CROSS-REFERENCE TO RELATED APPLICATION

This application is a continuation-in-part of copending application Ser. No. 459,912, filed Jan. 2, 1990, now abandoned.

BACKGROUND OF THE INVENTION

The present invention relates to novel therapeutic uses of a known compound, gabapentin, its derivatives, and pharmaceutically acceptable salts. The present invention concerns a method for treating neurodegenerative disorders in a mammal in need of such treatment.

Such neurodegenerative disorders are, for example, Alzheimer's disease, Huntington's disease, Parkinson's disease, and Amyotrophic Lateral Sclerosis.

The present invention also covers treating neurodegenerative disorders termed acute brain injury. These include but are not limited to: stroke, head trauma, and asphyxia.

Stroke refers to a cerebral vascular disease and may also be referred to as a cerebral vascular incident (CVA) and includes acute thromboembolic stroke. Stroke includes both focal and global ischemia. Also included are transient cerebral ischemic attacks and other cerebral vascular problems accompanied by cerebral ischemia. A patient undergoing carotid endarterectomy specifically or other cerebrovascular or vascular surgical procedures in general, or diagnostic vascular procedures including cerebral angiography and the like.

Other incidents are head trauma, spinal cord trauma, or injury from general anoxia, hypoxia, hypoglycemia, hypotension as well as similar injuries seen during procedures from embole, hyperfusion, and hypoxia.

The instant invention would be useful in a range of incidents, for example, during cardiac bypass surgery, in incidents of intracranial hemorrhage, in perinatal asphyxia, in cardiac arrest, and status epilepticus.

A skilled physician will be able to determine the appropriate situation in which subjects are susceptible to or at risk of, for example, stroke as well as suffering from stroke for administration by methods of the present invention.

U.S. Pat. No. 4,024,175 and its divisional U.S. Pat. No. 4,087,544 cover the compounds of the instant invention, methods for preparing them, and several uses thereof. The uses disclosed are: protective effect against cramp induced by thiosemicarbazide; protective action against cardiazole cramp; the cerebral diseases epilepsy, faintness attacks, hypokinesia, and cranial traumas; and improvement in cerebral functions. The compounds are useful in geriatric patients. The patents are hereby incorporated by reference.

The N-methyl-D-aspartic acid (NMDA) receptor is the best characterized of the receptor subtypes mediating the effects of the excitatory amino acid neurotransmitters. To date, the majority of compounds modulating activity at the NMDA receptor channel complex have been competitive or noncompetitive antagonists, i.e., D-APV (which is D-2-amino-5-phosphonovaleric acid) and MK-801 (which is dizocilpine or (+)-5-methy-10,11-dihydro-5H-dibenzo[a,d]cyclohepten-5,10-imine), respectively.

Recently it has been shown that NMDA responses in cultured cerebral neurons were greatly potentiated in the presence of submicromolar concentrations of glycine (Johnson and Ascher (1987), Nature 325, 529-531). Glycine potentiates the NMDA response in cultured mouse brain neurons. This site is strychnine insensitive, and therefore appears unrelated to the classical inhibitory glycine receptor. Since this glycine potentiation occurs at concentrations similar to those found in the extracellular solution surrounding neurons in vivo, the possibility exists that drugs may antagonize the actions of excitatory amino acids acting at the NMDA receptor by a selective action at the glycine modulatory site.

The overstimulation of NMDA receptors is thought to be involved in the etiology of several neurological disorders, i.e., epilepsy and cerebral ischemia. Evidence is also accumulating that the brain damage associated with anoxia, stroke, hypoglycemia, epilepsy and perhaps neurodegenerative illnesses such as Huntingdon's disease may be at least partially produced by excessive activation of NMDA receptors (Kemp, J.A., Foster, A.C., Wong, E.H.F. (1987). Non-competitive antagonists of excitatory amino acid receptors. Trends in Neurosciences 10(7), 294-298).

Since NMDA receptor activation is implicated in the generation of neurodegenerative diseases, and since glycine potentiates responses to NMDA, there is an enormous therapeutic potential for drugs which antagonize the actions of glycine at the modulatory site of the NMDA receptor.

The striatum receives a major neuronal input from the cortex, and this corticostriatal pathway is believed to use L-glutamate as its excitatory neurotransmitter. There is biochemical evidence for glutamate as a neurotransmitter in corticostriatal and corticothalamic fibers in the rat brain. (Fonnum, F., Storm-Mathisen, J., Divac, I. (1981), Neuroscience 6, 863-873.)

Previous in vitro studies have shown that excitatory amino acids are able to elicit responses from striatal neurons in brain slices and in dissociated culture. (Cherubini, E., Gerrling, P.L., Lanfumey, L., Stanzione, P. (1988). Excitatory amino acids in synaptic excitation of rat striatal neurons in vitro. J. Physiol. 400, 677-690; Ascher, P., Gregestovski, P., Nowal, L. (1988). NMDA activated channels of mouse central neurons in magnesium-free solutions. J. Physiol. 399, 207-226; Sprosen, T. S., Boden, P. R., Hughes, J. (1989). The development of excitatory amino acid responses in dissociated cultures of fetal rat striatum. European Neuroscience Association Abstract, Turin, Italy. 15.12 p43.)

Gabapentin has been shown to protect mice from seizures elicited by 4-aminobutanoic acid (GABA) synthesis or GABA receptor antagonists. Furthermore, it was found to prolong the latency of onset of seizures elicited by NMDA (Bartoszyk, G.D., Fritschi, E., Herrman, M., Satzinger, G. (1983). Indications for an involvement of the GABA-system in the mechanism of action of gabapentin. Naunyn-Schmiedeberg's Arc. Pharmacol. 322 R94). In mechanistic terms, the anticonvulsant action of gabapentin appears to be unrelated to an action on GABA systems, since it does not displace $GABA_A$ or $GABA_B$ binding and does not interfere with neuronal GABA uptake.

This study provides a possible mechanism for the anticonvulsant action of gabapentin, i.e., that it acts as a partial agonist at the glycine modulatory site of the NMDA receptor-channel complex. The partial agonist nature of gabapentin is reflected in its ability to antagonize the actions of glycine at the modulatory site, and its ability to potentiate response to NMDA (due to its agonist action at the glycine modulatory site, in the absence of exogenous glycine).

Since glycine potentiates responses to NMDA at physiological concentrations, gabapentin will act to antagonize the actions of endogenous glycine at the modulatory site and hence 'damp-down' the effects of NMDA receptor activation.

In addition to its anticonvulsant actions, these results indicate that gabapentin has additional therapeutic indications. Overstimulation of NMDA receptors has been implicated in the etiology of neuronal damage induced by anoxia, stroke, hypoglycemia, Huntington's disease, as well as epilepsy.

There is no disclosure in the above references to make obvious the present invention of novel uses of compounds of U.S. Pat. No. 4,024,175 to treat neurodegenerative disorders.

DETAILED DESCRIPTION

Following a stroke there is a massive and excessive release of the neurotransmitter glutamate. Glutamate acts on a type of glutamate receptor called the NMDA receptor to cause influx of calcium. Following excessive stimulation of NMDA receptors too much calcium flows into susceptible neurones to cause cell death. The hippocampus contains neurones particularly vulnerable to NMDA-induced toxicity. Thus the finding that Gabapentin blocks NMDA in the hippocampus is indicative of the use in stroke. Excessive convulsive activity as in Status Epilepticus causes neurodegeneration of some neurones in hippocampus—again by glutamate released onto NMDA receptors. Thus gabapentin is indicated in this form of neurodegeneration.

The present invention relates to novel methods of treating neurodegenerative diseases in a mammal in need of such treatment. The treatment comprises administering in unit dosage form an effective amount of a compound of formula

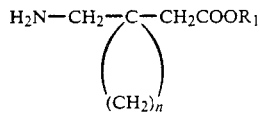

wherein $R_1$ is hydrogen or a lower alkyl and n is 4, 5, or 6 or a pharmaceutically acceptable salt thereof. The term lower alkyl includes straight or branched chain alkyl groups of up to eight carbon atoms.

Preferred compounds of formula I above include but are not limited to 1-aminomethyl-1-cyclohexane-acetic acid, ethyl 1-aminomethyl-1-cyclohexane-acetate, 1-aminomethyl-1-cycloheptane-acetic acid, 1-aminomethyl-1-cyclopentane-acetic acid, methyl 1-aminomethyl-1-cyclohexane-acetate, n-butyl 1-aminomethyl-1-cyclohexane-acetate, methyl 1-aminomethyl-1-cycloheptane-acetate, n-butyl 1-aminomethyl-1-cycloheptane-acetate, toluene sulfonate, 1-aminomethyl-1-cyclopentane-acetate, benzene-sulfonate, and n-butyl 1-aminomethyl-1-cyclopentane-acetate.

The most preferred compound is 1-aminomethyl-cyclohexane acetic acid (gabapentin).

Pharmaceutical compositions of the compound of the present invention or its salts are produced by formulating the active compound in dosage unit form with a pharmaceutical carrier. Some examples of dosage unit forms are tablets, capsules, pills, powders, aqueous and nonaqueous oral solutions and suspensions, and parenteral solutions packaged in containers containing either one or some larger number of dosage units and capable of being subdivided into individual doses. Some examples of suitable pharmaceutical carriers, including pharmaceutical diluents, are gelatin capsules; sugars such as lactose and sucrose; starches such as corn starch and potato starch, cellulose derivatives such as sodium carboxymethyl cellulose, ethyl cellulose, methyl cellulose, and cellulose acetate phthalate; gelatin; talc; stearic acid; magnesium stearate; vegetable oils such as peanut oil, cottonseed oil; sesame oil, olive oil, corn oil, and oil of theobroma; propylene glycol, glycerin; sorbitol; polyethylene glycol; water; agar; alginic acid; isotonic saline, and phosphate buffer solutions; as well as other compatible substances normally used in pharmaceutical formulations. The compositions of the invention can also contain other components such as coloring agents, flavoring agents, and/or preservatives. These materials, if present, are usually used in relatively small amounts. The compositions can, if desired, also contain other therapeutic agents.

The percentage of the active ingredient in the foregoing compositions can be varied within wide limits but for practical purposes it is preferably present in a concentration of at least 10% in a solid composition and at last 2% in a primary liquid composition. The most satisfactory compositions are those in which a much higher proportion of the active ingredient is present.

Routes of administration of the subject compound or its salts are oral or parenteral. For example, a useful intravenous dose is between 5 and 50 mg and a useful oral dosage is between 20 and 200 mg.

A unit dosage form of the instant invention may also comprise other compounds useful in the therapy of neurodegenerative diseases.

The advantages of using the compounds of formula I, especially gabapentin, in the instant invention include the relatively nontoxic nature of the compound, the ease of preparation, the fact that the compound is well tolerated, and the ease of IV administration of the drug. Further, the drug is not metabolized in the body.

The subjects as used herein are mammals, including humans.

The usefulness of compounds of formula I above and the salts thereof as agents for neurodegenerative diseases is demonstrated in standard pharmacological test procedures.

DESCRIPTION OF DRAWINGS

FIG. 3A–B shows voltage clamp records from a 14-day-old striatal neuron held at a holding potential of $-70$ mV. Inverted triangles indicate periods of rapid pressure ejection of NMDA (0.1 s/1 mM). Solid bars indicate periods of drug application via the perfusion system. Each record is separated by a constant time interval of four minutes.

FIG. 1 shows the potentiating effects of gabapentin on NMDA. The upper trace shows a control response to NMDA alone followed by a larger response produced by 10 $\mu$M gabapentin the presence of NMDA. The effects are reversed on washing, note lower trace.

FIG. 2A-C is a continuation from FIG. 1 and shows control NMDA response in the upper trace, the potentiating effect of glycine in the middle trace, and the blocking action of gabapentin in the bottom trace.

FIG. 3A-B shows the blocking effect by gabapentin on NMDA responses. In the upper traces the potentiating effect of gabapentin on basal NMDA responses is illustrated. In the lower traces the first response is to NMDA alone. The second shows the potentiating effect of glycine on NMDA responses. The third shows the blocking action of gabapentin on the glycine stimulated response, which shows recovery on washing.

FIG. 4A-B. Intracellular recording from a PVT neurone, membrane potential —60 mV. Upward deflections are action potentials produced on the depolarizing phase of an electrotonic current pulse (anode-break). The trace shows dose-dependent depolarizations to increasing concentrations of NMDA. Upper panel is the control dose-response curve obtained in normal ACSF. The lower trace was recorded in the presence of gabapentin (300 μM).

FIG. 6B. Data for the dose-response curve in 6a expressed as raw data points with the corresponding best fit for a hyperbolic function to show the noncompetitive nature of the gabapentin block of the NMDA response.

FIG. 7. Pen recorder trace of an intracellular recording from a CA1 hippocampal neurone. The top trace, FIG. 7A, the effect of NMDA (30, 10, and 50 μM) while the lower trace.

FIG. 8A. Dose response curves obtained for the mean depolarization brought about by NMDA of CA1 hippocampal neurones (n=3), in the absence (filled circles) and presence (filled squares) of gabapentin (300 μM).

FIG. 8B. Raw data for the graph in 8a, plotted with the corresponding best fit hyperbolic functions for the data, illustrating the noncompetitive nature of the gabapentin block of the NMDA response in hippocampus.

METHODS

Figure 1:
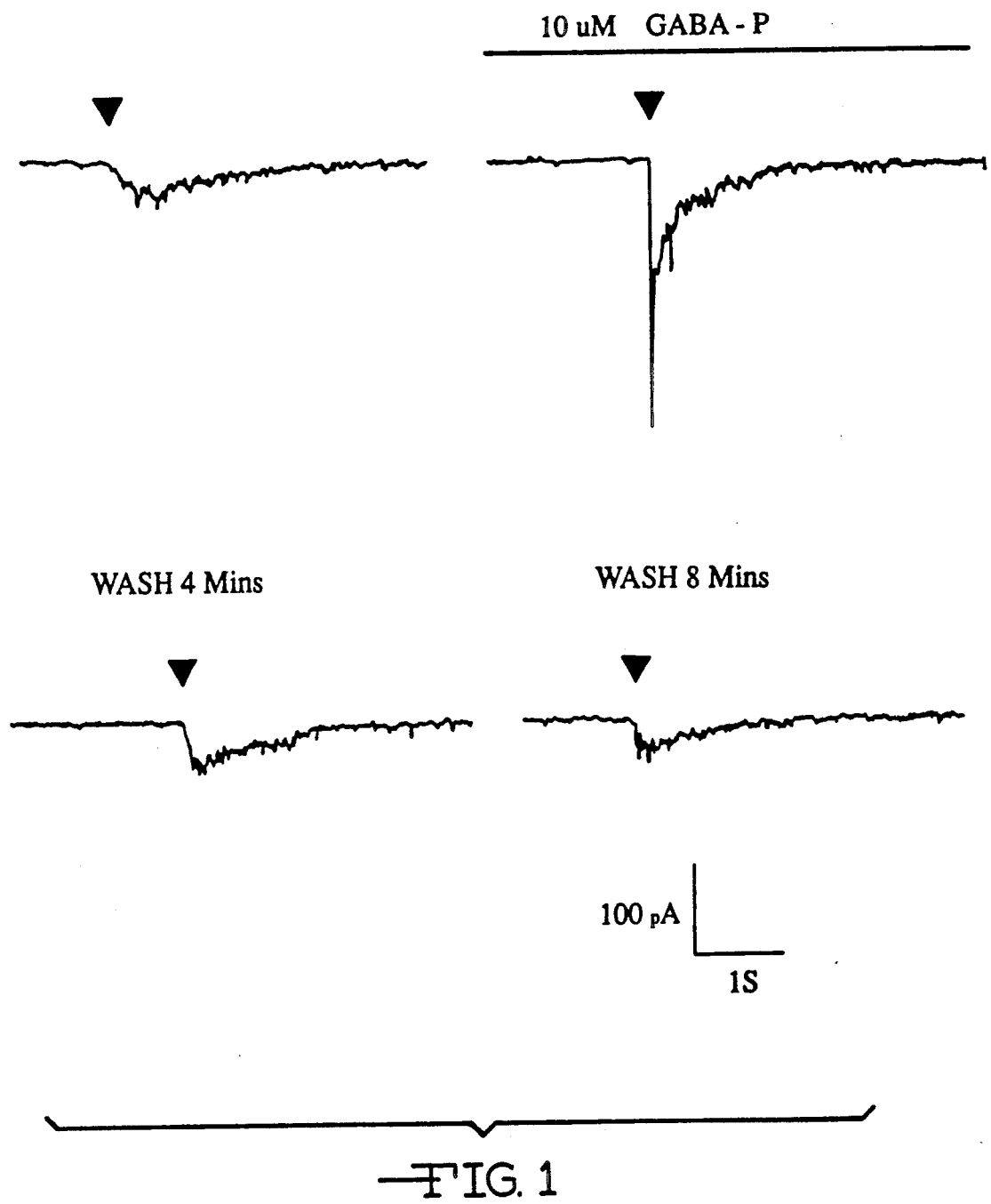
FIG. 1 and FIG. 2A–C are voltage-clamp records from a 13-day-old striatal neuron held at a holding potential of $-70$ mV. Inverted triangles indicate periods of rapid pressure ejection of NMDA (0.1 s/1 mM). Solid bars indicate periods of drug application via the perfusion system.
Figure 2A:
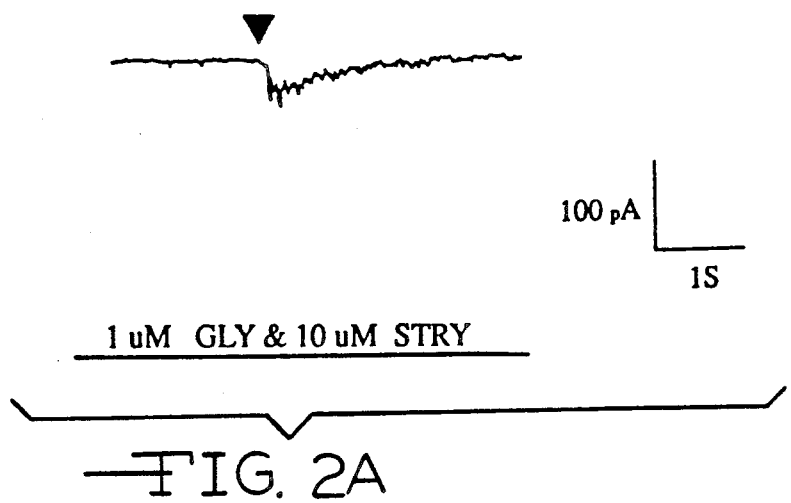
Figure 2B:
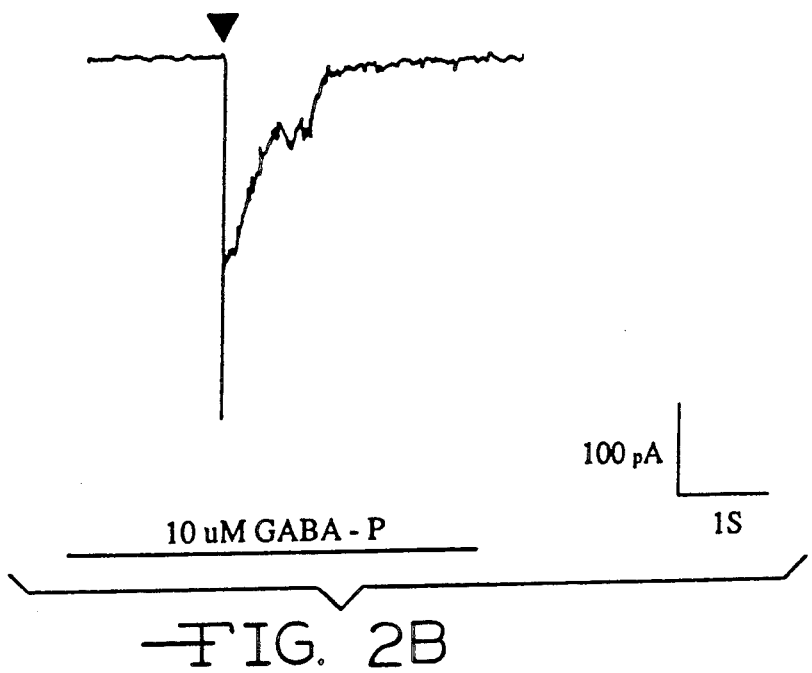
Figure 2C:
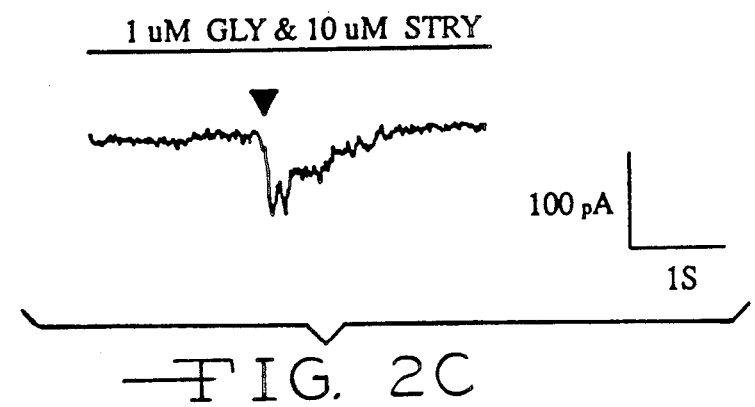

Whole-cell patch clamp techniques were employed to investigate the effects of the antiepileptic drug, gabapentin, upon the responses of striatal neurons in dissociated culture to NMDA.

Preparation of Dissociated Cultures of Fetal Rat Striatum

Striata were aseptically dissected from 16-day-old rat fetuses and mechanically triturated in enzyme-free Puck's saline (Gibco, UK). The resulting suspension was diluted to $1 \times 10^6$ cells/mL using freshly prepared medium. The medium was composed of Minimal essential medium with Earle's salts and included Fetal calf serum (5% v/v), Horse serum (5% v/v), L-Glutamine (2 mM), Insulin (5 g/mL), and HEPES (5 mM) buffer (all Gibco, UK).

The cells were plated onto Poly-L-ornithine (1.5 g/mL; Sigma) coated glass coverslips (diameter 13 mm) and incubated at 37° C. in a humidified atmosphere of 95% Air/5% $CO_2$.

After seven days, the media was replaced with freshly prepared media containing (+)-5-fluoro-deoxyuridine (10 μM; Sigma) to inhibit the proliferation of nonneuronal elements. Cultures were subsequently fed twice weekly.

Whole Cell Recording

Coverslips possessing striatal cultures were transferred to a Perspex recording chamber mounted on the stage of an inverted microscope (Nikon TMS) where they were continuously perfused (flow rate; 4 mL/min) with $Mg^{2+}$— free extracellular solution of the following composition (all mM); NaCl 126.0, KCl 2.5, $CaCl_2$ 2.0, $K_2HPO_4$ 1.2, $NaHCO_3$ 26.0, and Glucose 11.0.

Patch electrodes with ohmic resistances of 6-10 M Ω were filled with an intracellular solution of the following composition (all mM); CsF 140.0, $CaCl_2$ 0.5, NaCl 1.0, K-EGTA 5.0 and HEPES 10.0. All recordings were made at 20°-22° C. using a List EPC7 amplifier and the resulting signal was filtered at 10 KHz. Fast and slow transient capacity compensation was employed, and cells were voltage clamped at a holding potential of —70 mV, unless otherwise stated.

Drugs were dissolved to a known concentration in the extracellular solution and were applied via the perfusion system. NMDA was applied via the perfusion system, or by rapid pressure ejection. All drugs were obtained from Sigma, except gabapentin which was synthesized at Goedecke (Warner-Lambert) Germany.

Glycine (10–100-μM) produced a potentiation of the NMDA induced peak current on ten neurons tested, and this potentiation was strychnine insensitive (10–50 μM; Tables 1 and 2).

TABLE 1.

| | Potentiating Effect of Glycine |
|---|---|
| NMDA | Peak Inward Current (pA) 100% (n = 10) |
| NMDA + 1 μM Glycine + 10 μM Strychnine | 589 ± 156% (n = 10) |

Bath application of gabapentin (10 μM) produced a potentiation of the NMDA-induced current, which readily reversed upon washing with drug-free extracellular solution for four minutes.

TABLE 2.

| | Potentiating Effect of Gabapentin; i.e., Partial Agonist |
|---|---|
| NMDA | Peak Inward Current (pA) 100% (n = 4) |
| NMDA + 10 μM GABA-P | 305 ± 88% (n = 4) |
| NMDA + 'wash' | 106 ± 9% (n = 4) |

Concurrent application of gabapentin (10 μM) with glycine (1 μM) and strychnine (10 μM) produced an antagonism of the glycine-induced potentiation of the NMDA-induced current. This antagonism by gabapentin was readily reversed by washing with drug-free extracellular solution for four minutes.

TABLE 3.

| | Antagonism Effect of Gabapentin on Glycine |
|---|---|
| NMDA | Peak Inward Current (pA) 100% (n = 4) |
| NMDA + 1 μM Glycine + 10 μM Strychnine | 713 ± 260% (n = 4) |
| NMDA + 1 μM Glycine + 10 μM Strychnine + 10 μM GABA-P | 201 ± 24% (n = 3) |
| 'wash' NMDA + 1 μM Glycine + 10 μM Strychnine | 257 ± 418% (n = 3) |

Bath application of NMDA (100 μM) produced a sustained inward current (Table 3) which was markedly potentiated by application of glycine (1 μM). Gabapentin (10 μM) produced a reversible potentiation of the NMDA-induced current in the absence of glycine, but an antagonism of the glycine-potentiated NMDA current (Table 3).

Effects of gabapentin on NMDA-induced depolarizations of hippocampal and thalamic neurones

In Vitro

Intracellular recordings were made from neurones of either paraventricular thalamus (n = 8, 7 slices) or CA1 region of the hippocampus (n = 5, 5 slices) contained in 400 μM rat brain slices. NMDA applied via the perfusion system, produced a concentration-dependent depolarization of all neurones tested. In every case but one, control response to NMDA was reduced by a concomitant application of gabapentin (300 μM). The concentration-response curves for NMDA in the presence and absence of gabapentin show a noncompetitive interaction of gabapentin with NMDA receptor-channel complex.

Methods

Coronal slices of rat brain at the level of the ventromedial hypothalamus were chosen since these contain both hippocampus and paraventricular thalamus (PVT). Slices were perfused in normal (1.3 mM magnesium) artificial cerebrospinal fluid (ACSF) at 3 mL/min. Conventional intracellular recording techniques were employed, using 1M potassium acetate-filled electrodes pulled on a Brown-Flaming microelectrode puller type P-87. The use of current-clamp techniques meant that control of membrane potential was not optimal and so whenever possible neurones were chosen which possessed resting membrane potentials of around −60 mV, to allow pooling of results, and negate any influence of the voltage-dependent block of magnesium ions on the results.

Drugs were made up as stock solutions in distilled water (NMDA 50 mM; gabapentin 100 mM) and stored frozen prior to use. The required concentrations of each drug were obtained by direct dilution with ACSF at the time of the experiment. Control dose-response curves for NMDA were obtained either in the presence or absence of tetrodotoxin (TTX). NMDA was applied to a 30-second period, with at least five minutes between successive doses. Gabapentin was added to the same NMDA-containing solutions and the dose-response curves repeated. Experiments were also performed using repeated single doses of NMDA to ensure that the effects of gabapentin were not due to rundown of the NMDA response.

Results

Figure 4A:
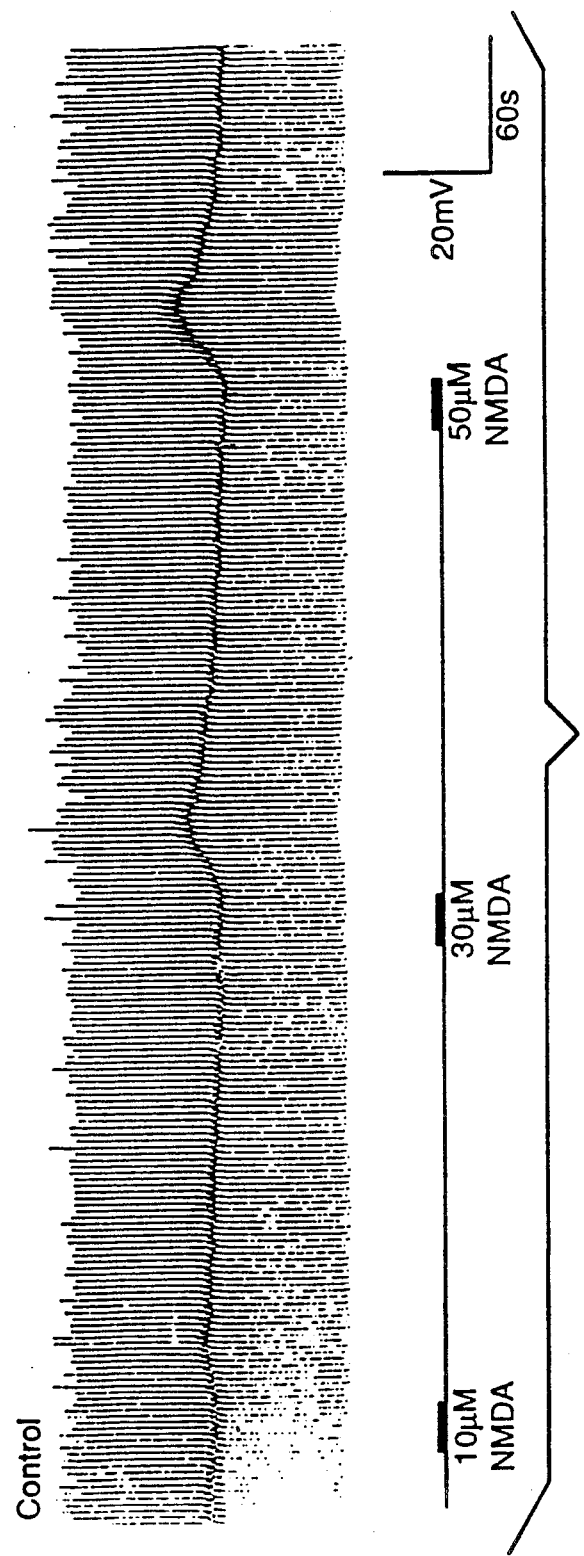

Thalamus. NMDA produced a concentration-dependent depolarization of PVT neurones. This is illustrated in FIG. 4. When the experiment was repeated in the presence of gabapentin (300 μM) the response to high (30 to 50 μM) concentrations of NMDA was reduced.

Figure 5A:
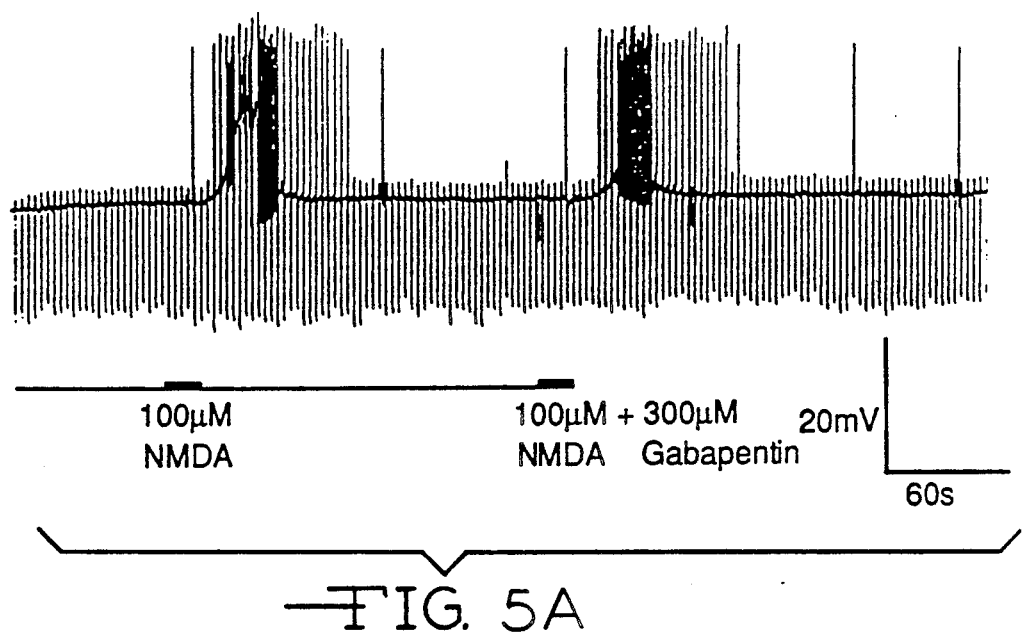
FIG. 5A-C. Pen recorder trace taken from a PVT neurone. The figure is a continuous pen recording from a single neurone. Trace a shows the effect of 100 μM NMDA and the subsequent reduction of the large depolarization by gabapentin (300 μM). In the middle panel, b, TTX was added to block sodium-dependent action potential firing. The NMDA-induced depolarization is now clearly seen (note also the presence of calcium-dependent action potentials on the repolarizing phase of the response). The NMDA depolarization was reduced in the presence of gabapentin, an effect which reversed on removal of gabapentin. Indeed, the initial NMDA response was enhanced following removal of gabapentin in this example. Trace c was taken immediately after and shows the return of the NMDA response to control amplitude.
Figure 5B:
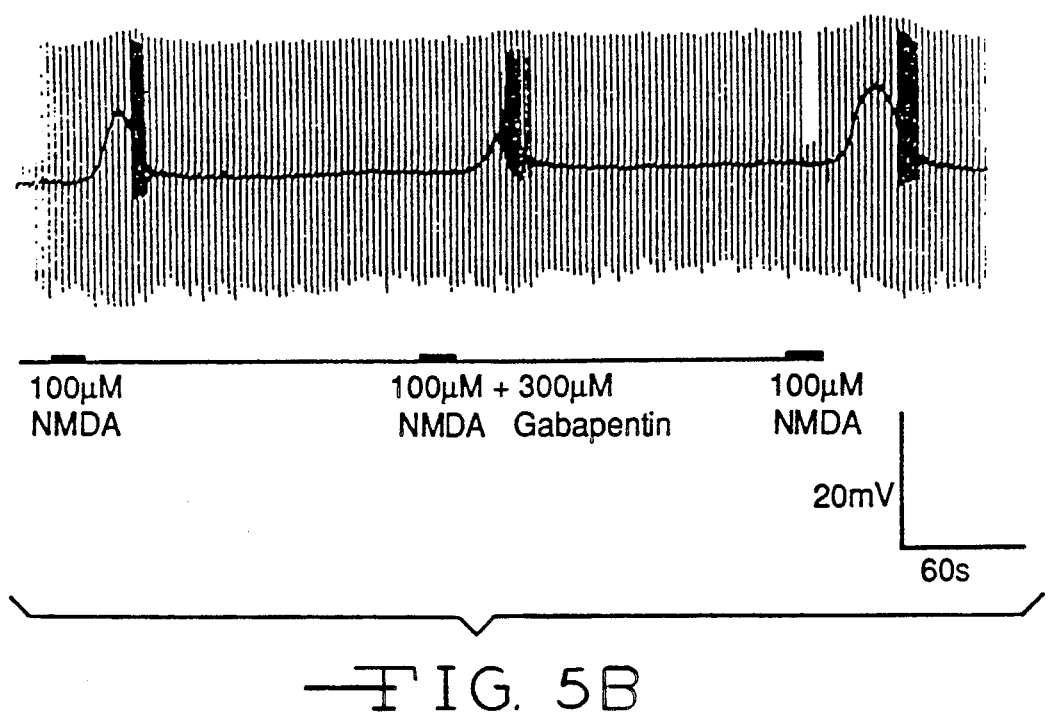
Figure 5C:
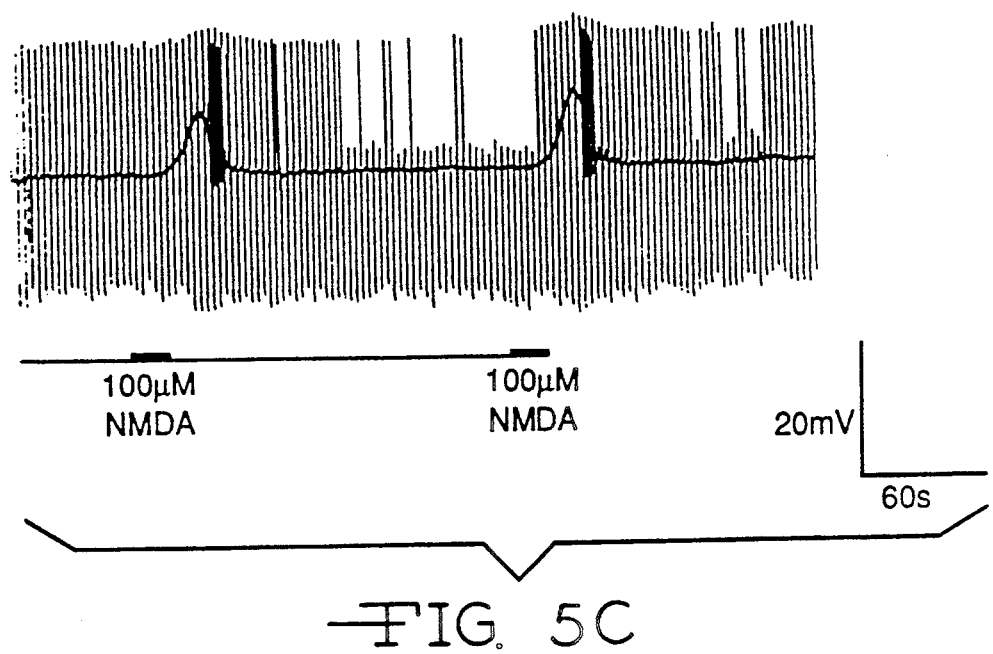

FIG. 5 illustrates the effects of a 30s application of 100 μM NMDA to thalamic neurones in the absence and presence of gabapentin (300 μM). The large depolarization caused by NMDA was much reduced by the anticonvulsant. The NMDA depolarization could be seen more clearly following TTX treatment to abolish sodium-dependent action potentials. Addition of gabapentin reduced the depolarization by some 60% (FIG. 5). This effect was readily reversed, subsequent applications of NMDA giving approximately the same amplitude depolarization.

Figure 6A:
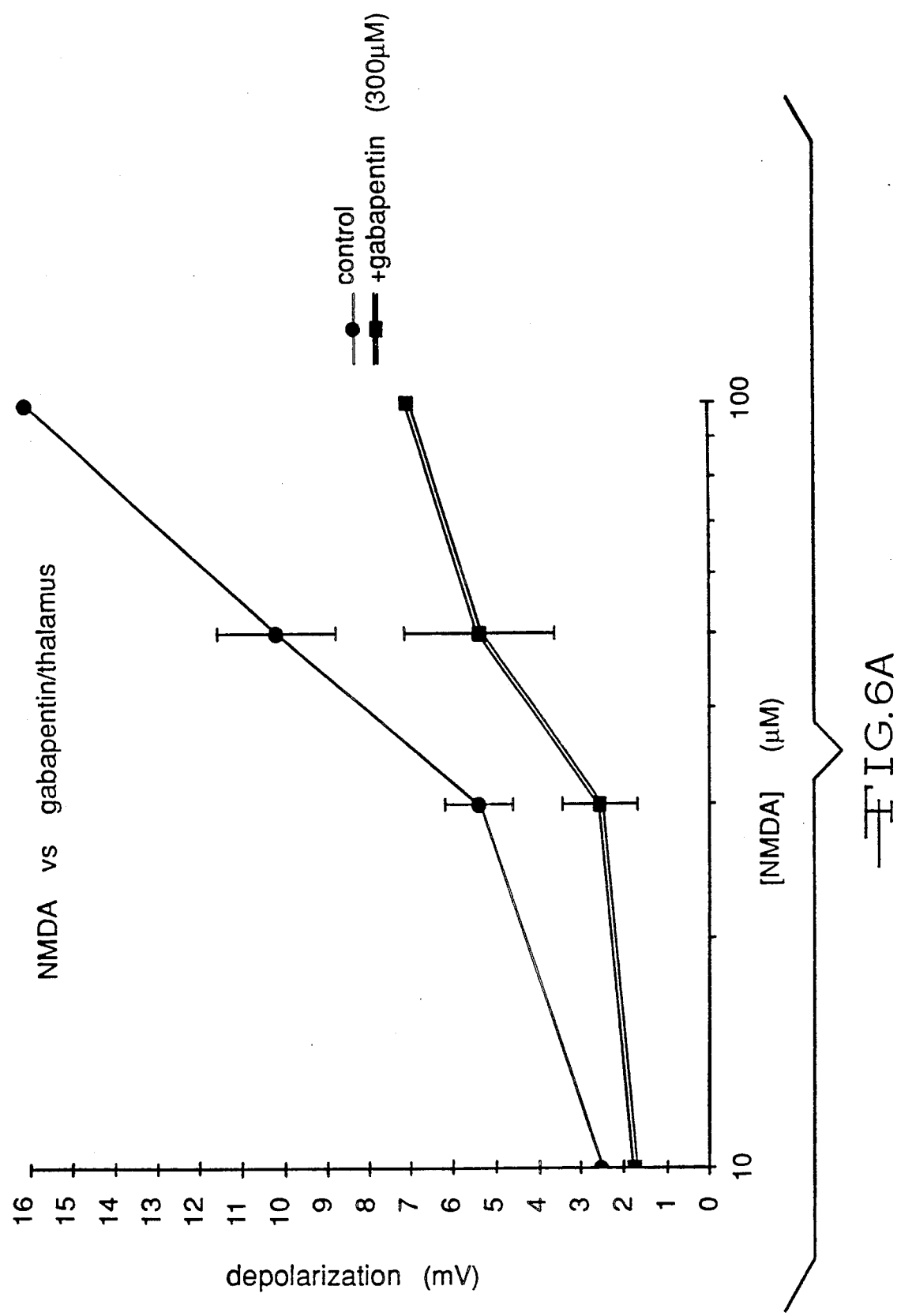
FIG. 6A. Dose-response curves plotted for mean NMDA depolarization in the absence (filed circles) and presence (filled squares) of gabapentin. The points are the mean of five separate experiments, with the exception of those for 100 μM NMDA, using recording made from PVT neurones.

FIGS. 6A and 6B show dose-response curves obtained for NMDA in the absence and presence of gabapentin (300 μM) from five individual neurones. The results in FIG. 6A are expressed as mean+/−sem, while FIG. 6B gives the same data in raw form together with best fit curves for a standard hyperbolic function.

Figure 7B:
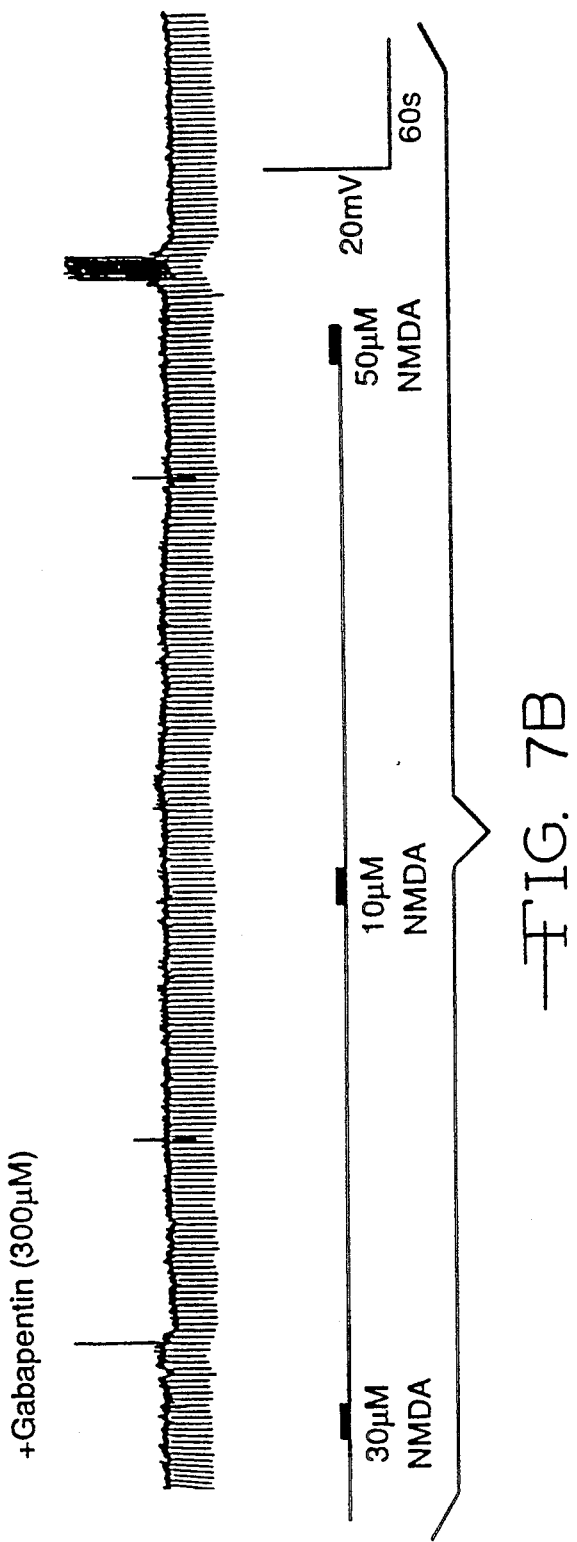
FIG. 7B, is a continuation of the recording showing the re of the NMDA response by gabapentin (300 μM).

CA1 Hippocampus. The experiments were repeated on recordings made from CA1 hippocampal neurones. Again, the effect of gabapentin was seen as a reduction in the NMDA-induced depolarization (FIG. 7) becoming more evident as the concentration of NMDA was increased.

FIGS. 8A and 8B present the data from all dose-response studies expressed as either mean+/−sem (FIG. 8A) or best fit hyperbolic functions to the raw data (FIG. 8B).

Examples of formulations of the subject compounds or salts thereof are illustrated by the following examples.

EXAMPLE 1

Injectables 1 mg to 100 mg/mL

Gabapentin
Water for Injection USP q.s.

The compound or a suitable salt thereof is dissolved in water and passed through a 0.2-micron filter. Aliquots of the filtered solution are added to ampoules or vials, sealed and sterilized.

EXAMPLE 2

Capsules 50 mg, 100 mg, 200 mg, 300 mg or 400 mg
Gabapentin, 250 g
Lactose USP, Anhydrous q.s. or 250 g
Sterotex Powder HM, 5 g Combine the compound and the lactose in a tumble blend for two minutes, blend for one minute with the intensifier bar, and then tumble blend again for one minute. A portion of the blend is then mixed with the Sterotex powder, passed through a #30 screen and added back to the remainder of the blend. The mixed ingredients are then blended for one minute, blended with the intensifier bar for 30 seconds, and tumble blended for an additional minute. The appropriately sized capsules are filled with 141 mg, 352.5 mg, or 705 mg of the blend, respectively, for the 50 mg, 125 mg, and 250 mg containing capsules.

EXAMPLE 3

Tablets 5 mg, 100 mg, 200 mg, 300 mg, 400 mg, 500 mg or 600 mg
Gabapentin, 125 g
Corn Starch NF, 200 g
Cellulose, Microcrystalline. 46 g
Sterotex Powder HM, 4 g
Purified Water q.s. or 300 mL Combine the corn starch, the cellulose, and the compound together in a planetary mixer and mix for two minutes. Add the water to this combination and mix for one minute. The resulting mix is spread on trays and dried in a hot air oven at 50° C. until a moisture level of 1 to 2 percent is obtained. The dried mix is then milled with a Fitzmill through a #RH2B screen, and added back to the milled mixture and the total blended for five minutes by drum rolling. Compressed tablets of 150 mg, 375 mg, and 750 mg, respectively, of the total mix are formed with appropriate sized punches the 50 mg, 125 mg, or 50 mg containing tablets.

I claim:

1. A method for treating neurodegenerative diseases which comprises administering a therapeutically effective amount of a compound of formula

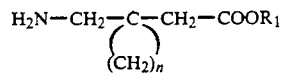

wherein $R_1$ is hydrogen or a lower alkyl and n is 4, 5, or 6 or a pharmaceutically acceptable salt thereof, in unit dosage form, to a mammal in need of said treatment.

2. A method according to claim 1 wherein the neurodegenerative disease is stroke.

3. A method according to claim 1 wherein the degenerative disease is Alzheimer's disease.

4. A method according to claim 1 wherein the degenerative disease is Huntington's disease.

5. A method according to claim 1 wherein the degenerative disease is Amyotrophic Lateral Sclerosis.

6. A method according to claim 1 wherein the degenerative disease is Parkinson's disease.

7. A method according to claim 1 wherein the compound is gabapentin or a pharmaceutically acceptable salt thereof.

8. A method according to claim 1 wherein an individual dose is 5 mg to 50 mg parenterally or 50 to 600 mg enterally of the compound or a pharmaceutically acceptable salt thereof is administered.

* * * * *